United States Patent
Berlad

Patent Number: 6,140,650
Date of Patent: Oct. 31, 2000

[54] CALIBRATION OF PET CAMERAS

[75] Inventor: Gideon Berlad, Haifa, Israel

[73] Assignee: Elgems Ltd., Tirat Hacarmel, Israel

[21] Appl. No.: 09/013,044

[22] Filed: Jan. 26, 1998

[30] Foreign Application Priority Data

Nov. 27, 1997 [IL] Israel ........................................ 122357

[51] Int. Cl.$^7$ .................................................. G01T 1/166
[52] U.S. Cl. .................. 250/363.09; 250/363.03
[58] Field of Search ........................... 250/363.09, 363.03

[56] References Cited

U.S. PATENT DOCUMENTS

| | | |
|---|---|---|
| 4,424,446 | 1/1984 | Inbar et al. . |
| 4,588,897 | 5/1986 | Inbar et al. . |
| 5,481,115 | 1/1996 | Hsieh et al. ........................ 250/363.04 |
| 5,689,115 | 11/1997 | Balan et al. . |
| 5,818,050 | 10/1998 | Dilmanian et al. ................. 250/363.09 |

FOREIGN PATENT DOCUMENTS

WO 98/19179  5/1998  WIPO .

*Primary Examiner*—Constantine Hannaher
*Attorney, Agent, or Firm*—Fenster & Company Patent Attorneys, Ltd.

[57] ABSTRACT

A method of calibrating a PET (Positron Emission Tomograph) scanner includes:

acquisition of data from a plurality of coincidence radiation events, using at least one detector; and determination of values for a set with at least one calibration factor, which factor affects an analytically defined calibration criterion. Preferably, the detector has at least one rotating planar detector and the acquisition of data includes acquiring data from a plurality of rotational positions of the detector.

34 Claims, 2 Drawing Sheets

Microfiche Appendix Included
(2 Microfiche, 146 Pages)

CALIBRATION OF PET CAMERAS

MICROFICHE APPENDIX

Attention is directed to a microfiche appendix attached hereto, having two fiches and a total of 146 frames and which contains appendixes A and B, comprising software for performing some of the preferred embodiments of the present invention.

COPYRIGHT NOTICE

A portion of the disclosure of this patent document contains material which is subject to copyright protection. The copyright owner has no objection to facsimile reproduction by anyone of the patent document or the patent disclosure, as it appears in the Patent and Trademark Office patent file or records, but otherwise reserves all rights whatsoever.

FIELD OF THE INVENTION

The present invention relates to nuclear medicine imaging systems and in particular to the calibration of imaging systems with moving detectors.

BACKGROUND OF THE INVENTION

Nuclear medicine imaging systems, also known as gamma cameras, are used to determine the distribution of a radio pharmaceutical which is introduced into the body of the patient. Gamma cameras fall into two broad categories, those which determined the occurrence of a radioactive event based on the acquisition of a single photon at a detector and those which determine the presence of such an event based on the coincident acquisition of photons at two detectors on opposite sides of the patient. The first category includes planar gamma cameras and SPECT cameras while the second category includes PET (Positron Emission Tomograph) in which the radioactive events generate two gamma rays which are emitted in opposite directions from the position of the event. The path of these directions is referred to as the line of flight (LOF) (or LOR—line of reaction) and is determined as the line connecting two detected interactions on detectors situated on opposite sides of the patient.

Another way of categorizing gamma cameras is by the type of image which is finally constructed from the acquired data. One category of image is a planar image. The other type is a tomographic (three-dimensional) image.

Gamma cameras of all types require calibration. Calibrations can relate to corrections for the intrinsic lack of accuracy of the detectors themselves. Such corrections include energy correction, linearity correction, rate correction and sensitivity corrections. Exemplary corrections of this type are described, for example in U.S. Pat. Nos. 4,424,446 and 4,588,897, the disclosures of which are incorporated herein by reference. At least some of these corrections are generally necessary for most types of detectors whether they are used for acquiring planar images or for acquiring tomographic images.

When data is acquired for the construction of tomographic images utilizing non-stationary detectors, such as single or dual detectors which rotate about the patient and acquire data for SPECT images, the position of the detectors as they rotate must also be determined so that the information from the various views of the patient may be properly associated in forming the tomographic image. Generating corrections for sagging and other unwanted movement of the detectors as they rotate about the patient is described, for example in U.S. patent application Ser. No. 08/562,375, filed Nov. 24, 1995, now U.S. Pat. No. 5,689,175 the disclosure of which are incorporated herein by reference.

PET images, which are one class of tomographic images, are generally acquired using stationary rings of detectors surrounding the patient. Thus, in general, PET imagers of this type do not need position correction of the type required by SPECT imagers.

The present invention, in some aspects thereof, is concerned with the calibration of gamma camera systems which utilize two or more planar detectors, placed on opposite sides of the patient, to acquire data for the construction of PET images. During acquisition, these detectors are rotated around the patient so that data from a plurality of detector positions can be acquired. Methodology for the construction of PET images is well known in the art. In the past, correction factors for the system operating as a single photon imager and geometrical alignment factors for SPECT were determined. Due to the uncollimated nature of coincident data acquisition, the calibration method applied to parallel hole SPECT do not generally apply to PET. In one exemplary PET calibration process, a virtual collimation process is executed by rebinning the coincidence data into parallel projections. However, this rebinning process is itself dependent on a prior knowledge of the proper calibration parameters. Consequently, in this exemplary PET calibration process, the calibration parameters had to be determined in an indirect manner. In particular, it was determined that a correction for dx1+dx2 was required (where dx1 and dx2 are the transaxial positions on the detector). This correction was derived by acquiring an image of a line source and reconstructing the image. The correction was varied until the image was optimized. This process was repeated several times until a maximal improvement was achieved.

SUMMARY OF THE INVENTION

One object of some embodiments of the present invention is the provision of a system for the geometric calibration of PET systems having multiple detector heads, preferably, rotating detectors.

One aspect of some embodiments of the present invention relates to using point sources for acquiring calibration data, rather than sources of higher dimensions, such as line sources.

Another aspect of some embodiments of the present invention relates to defining an analytical criterion for the quality of the calibration. The term analytical is used to refer to any type of criterion which can be automatically and objectively determined from the data, without resort to human input, including numerical criteria and those defined using analytical functions. Such a criterion is preferably applied instead of—or in addition to—subjective image quality criteria. One preferred criterion is the RMS distance of LOF from a point source. As can be appreciated, this criterion is especially suitable for automatic manipulation of data, as opposed to image quality criteria, which typically require some type of manual input. As a result, the calibration data need only be acquired once, and then it can be automatically manipulated. It should also be noted that a point source is generally more suited than a line source for this type of automatic calibration, since there is no ambiguity regarding the origin of the radiation. Alternatively, a line source may be used, especially in combination with a collimator.

In preferred embodiments of the present invention, the camera is first corrected for mechanical/geometric alignment errors as for a SPECT camera and/or for errors relating to the detection of single photons, such as linearity errors.

PET event data is then collected from, preferably, a point source and optionally, a plurality of such sources. In a preferred embodiment of the invention, one or more spaced point sources of positron annihilation generated emissions is placed within the space which will contain the patient. Each of these sources will generate gamma ray pairs along LOFs in many directions. Each LOF passes through a point source. Due to distortions in the geometry, some static, some dependent on rotation angle and some due to the finite resolution of the detectors, the LOFs calculated from the detected interactions on the detectors and based on the geometry will not pass through the same point, even though they actually originate at the same point.

In the preferred embodiment of the invention, the LOF for each detected event pair is calculated. As indicated above, the calculated LOF will pass some small distance from the source. This distance is calculated for each LOF and the correction factors are calculated such that the root mean square error of the distances is minimized. Preferably, stray LOFs are eliminated, for example, by eliminating all LOFs which are more than two or three standard deviations from the source. Stray LOFs usually originate from scattered photons or random occurrences. An exact knowledge of the position of the point source is not necessary, since the mean position of the source may be determined from the near crossing points of the LOF, for example by minimizing the mean square distances while varying the estimated position of the source.

In a preferred embodiment of the invention, the correction factors which generate a minimal RMS error are determined using a search technique.

As indicated above, more than one source can be used. If the sources are sufficiently spaced, it will be obvious which LOFs are associated with which source, especially for axially spaced sources. It should be appreciated, that the better the initial single-photon type correction, the denser such sources can be. The use of such multiple sources is useful for improving the accuracy of the determination of the correction factors since it is generally true that any insensitivity of one of the correction factors for a given source position will not apply to two or more sources.

This PET data which is preferably collected in list mode, so that the same data may be used for multiple iterations of correction factor values.

A large number of correction factors can be determined using this method. Some of these correction factors are dependent on rotational position and some are not. However, the minimization process is simplified if only those factors which are sizable and/or those which contribute to errors in the PET image for a particular system configuration are corrected for. Furthermore, errors which can be corrected using SPECT and/or single photon correction factors should be corrected first. In many instances, such corrections of particular errors is sufficient for correcting PET images. It has been found, for example, that at least to first order for a camera properly aligned for SPECT, no additional corrections as a function of rotation angle need be made for PET.

In order to better understand the geometric alignment problem and its associated calibration factors, consider the line of flight (LOF) of a gamma ray pair impinging on two detectors of a rotatable PET system. Each of the detectors has its own planar coordinate system; thus one of the two gamma rays is detected at location (x1, y1) on detector D1 while its counterpart is detected at (x2, y2) on detector D2, with y1 and y2 being substantially parallel to the axis of rotation of the detectors about the patient and x1 and x2 being perpendicular to y1 and y2 and thus also orthogonal to the axis of rotation.

The LOF is defined by its end points $\{x1, y1, z1=r\}$ and $\{x2, y2, z2=-r\}$ where r is the radius of rotation of the of the detectors D1 and D2. In a perfectly aligned system the origins of the x, y coordinate systems on D1 and D2 are aligned with each other and with the center of the axis of rotation; and the radius of rotation is equal for the two detectors and is not a function of the angle of rotation. Furthermore, in a perfectly aligned system, lines connecting $\{x1=0, y1\}$ and $\{x2=0, y2\}$ will intersect the axis of rotation.

In general, the two detectors can suffer from a number of types of misalignment. These are, in general, in order of importance:

1) Three in-detector plane displacements, dx1, dx2, dy, aligning both detector origins with a single point along the axis of rotation.

2) Two in-detector plane rotation angles, a1 and a2, around the x1, x2 axes, aligning y1 and y2 with each other.

3) Two radial displacements, dr1 and dr2, correcting for small differences in radius of rotation of the detectors and for the effective depth of interaction of the 511 keV electrons which are characteristic of the positron events of PET.

As indicated above, more corrections are theoretically required to fully correct the positions of the detectors in space. For example, for each detector four corrections are required (for example dy, dx, dR and a or dy, dR, a and b, the other rotation of the detector) to align a single detector to the axis such that the centers coincide with the center of the axis and so that the radius goes, perpendicularly, through the origin. Thus, to align two detectors with the axis you need 8 corrections. However, this does not assure that the two detectors will be parallel to each other. This requires a ninth correction. Furthermore, each of these corrections may be different for each rotational position of the detectors.

However, as indicated above, in many cases, depending on the geometry of the PET system, most of these errors are either adequately corrected for utilizing the SPECT alignments and/or the single photon corrections or are not important in the construction of PET images.

There is therefore provided in accordance with a preferred embodiment of the invention, a method of calibrating a PET (Positron Emission Tomograph) scanner, comprising:

acquiring data from a plurality of coincidence radiation events, using at least one detector; and determining values for a set comprising at least one calibration factor, which factor affects an analytically defined calibration criterion.

Preferably, said at least one detector comprises at least one rotating planar detector and wherein acquiring data comprises acquiring data from a plurality of rotational positions of the at least one detector.

Preferably, said at least one rotating detector comprises two rotating detectors and wherein said rotating detectors rotate around an axis and wherein said at least one factor comprises a sum of linear translations of said two detectors along a transaxial direction.

In a preferred embodiment of the invention, said radiation emanates from a point source and impinges on said detectors at input angle from said point source, relative to a line perpendicular to said axis and connecting said point source and comprising rejecting events response to said input angle.

Preferably, said input angle comprises an axial component and wherein said rejecting comprises rejecting responsive to said axial component. Alternatively or additionally, said input angle comprises a transaxial component and wherein said rejecting comprises rejecting responsive to said transaxial component.

Preferably, the method includes limiting the allowed input angles, responsive to event statistics of the acquired data.

In a preferred embodiment of the invention, the method includes positioning one or more point sources in said PET scanner, wherein said radiation events occur substantially inside said point sources.

Alternatively or additionally, the method includes performing single-photon type corrections on said PET scanner, prior to acquiring said data.

Alternatively or additionally, the method includes estimating a position of a source of at least some of said radiation events from said acquired data.

Preferably, said determining values comprises determining values responsive to said estimated position.

In a preferred embodiment of the invention, the criterion is an error criterion and wherein determining comprises optimizing said at least one factor to minimize the error criterion.

Preferably, optimizing at least one factor comprises:

optimizing said first factor and at least a second factor; and clamping said second factor to zero, responsive to the determined values thereof.

Alternatively or additionally, optimizing comprises performing an iterative search.

In a preferred embodiment of the invention, determining comprises determining said value without user input.

Alternatively or additionally, determining comprises:

determining said values using said data; and repeating said determining with a subset of said data, said subset not including at least some stray radiation events, said repeating utilizing said determined values in said repeated determination.

There is also provided in accordance with a preferred embodiment of the invention, a method of calibrating a focused single-photon system, comprising:

acquiring data from a plurality of radiation events, generated by a radiation source, using at least one rotating detector; and determining values for a set comprising at least one calibration factor, which factor affects an analytically defined calibration criterion, wherein determining said values comprises optimizing the calibration with respect to at least one of a center of rotation of said system, a focal location of said system and a location of the radiation source.

Preferably, said optimization comprises minimizing a calculated distance between a location of said radiation source and a line connecting said focal point and said at least one detector. Alternatively or additionally, said radiation source is a point source.

Alternatively or additionally, said focused system has a fan geometry. Alternatively or additionally, said focused system has a cone geometry.

There is also provided in accordance with a preferred embodiment of the invention, a method of calibrating an event counting medical imaging system, comprising:

acquiring data from a plurality of radiation events, using at least one detector; and determining values for a set comprising at least one calibration factor; and repeating said determining with a subset of said data, said subset not including at least some stray radiation events, utilizing said determined values in said repeated determination.

Preferably, said factor affects an analytically defined calibration criterion.

There is also provided in accordance with a preferred embodiment of the invention a method of measuring volumetric linearity of a nuclear medicine system, comprising:

positioning at least one radiation point source;

acquiring data from a plurality of radiation events, generated by said at least one point source, using at least one detector;

determining a location of said point source from said radiation events;

repeating said positioning, said acquiring and said determining for a plurality of positions of said radiation source; and comparing said determining locations and the positions of the point source.

Preferably, said point source comprises a positron source. Preferably, said radiation events comprise coincidence events.

There is also provided in accordance with a preferred embodiment of the invention, a method of determining a potential resolution, along at least one dimension, of an event counting nuclear medicine system, comprising:

acquiring data from a plurality of radiation events, generated by a radiation source, using at least one detector; and determining a calculated distance, in said dimension, between a path determined for a radiation event and the location of the radiation source, for a plurality of radiation events.

Preferably, said radiation events comprise coincidence events. Preferably, said determined path connects determined interaction positions of components of a single coincidence event.

Alternatively, said determined path connects a focal location of a collimator associated with said at least one detector and an interaction position of said radiation event on said detector.

In a preferred embodiment of the invention, said radiation source comprises at least one point source.

Alternatively or additionally, said at least one detector rotates around an axis. Preferably, said at least one dimension comprises a transaxial dimension. Alternatively or additionally, said at least one dimension comprises an axial dimension.

BRIEF DESCRIPTION OF THE DRAWINGS

For a more complete understanding of the invention, reference should be made to the following detailed description which is given in conjunction with the accompanying drawings, of which.

DETAILED DESCRIPTION OF PREFERRED EMBODIMENTS

Figure 1:
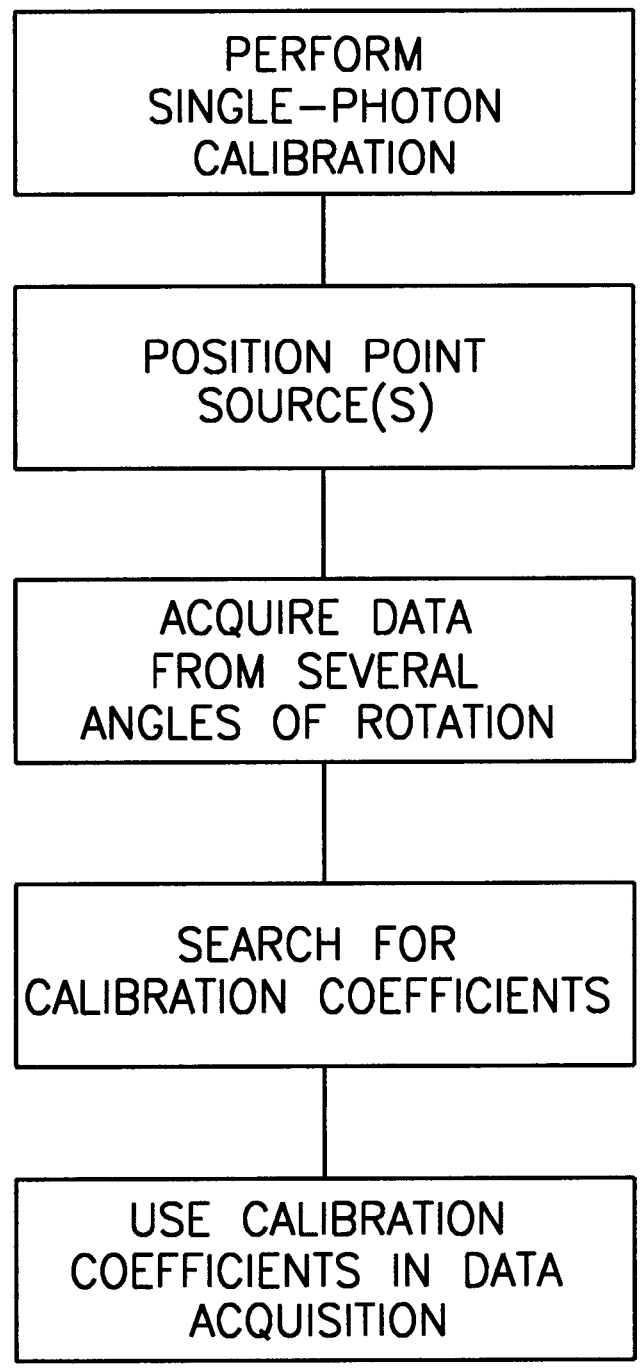
FIG. 1 is a flowchart of a method of PET scanner calibration, in accordance with a preferred embodiment of the invention.

FIG. 1 is a flowchart of a method of PET scanner calibration, in accordance with a preferred embodiment of the invention. The type of calibration shown in FIG. 1 is especially suited for PET scanners which utilize pairs of rotating planar detectors, although it may also be used for the more standard stationary ring type detectors, except that for stationary detectors, the third step may be omitted. Even though the requirements for SPECT imaging are different than those for PET imaging, calibrating a system for SPECT imaging is a good starting point for calibration for PET. Thus, in a preferred embodiment of the invention, SPECT alignment and single-photon corrections are performed first, before any other types of corrections are determined. Generally, SPECT calibration will correct for errors associated with sag and twist of a single detector, while single photon calibration will determine the coordinate mapping of a single detector. However, such calibration does not usually address corrections of the relative orientation of two detectors.

One or more point sources are then positioned inside the imaging volume. Although even a single point source may be used, preferably a plurality of point sources are used, to make the calibration more precise over a larger imaging volume. Each of the point sources is preferably a source of positrons, surrounded by a material with which most of the positrons will interact to create a gamma ray pair. Thus, it can be assumed that most of the gamma ray pairs detected by the PET system during the calibration originate inside one of the point sources.

Figure 2:
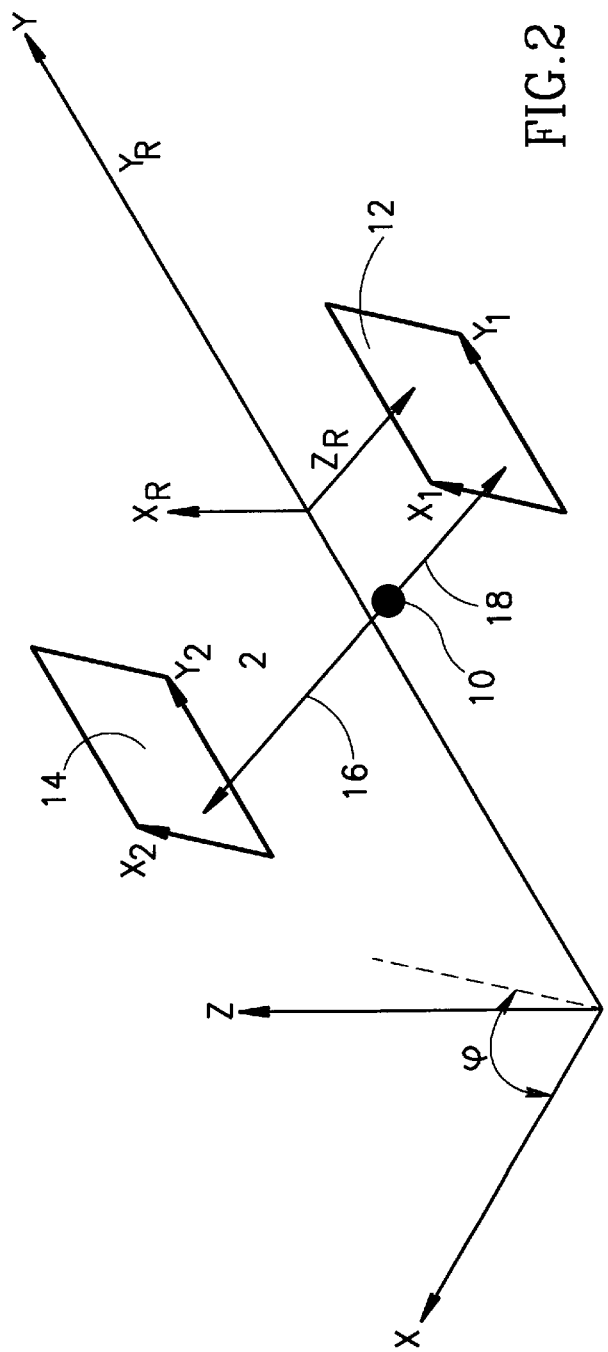
FIG. 2 is a schematic diagram of the geometry of a point source and a pair of rotating detectors, in accordance with a preferred embodiment of the invention.

FIG. 2 is a schematic diagram of the geometry of a point source 10 and a pair of rotating detectors 12 and 14, in accordance with a preferred embodiment of the invention. Although only one pair of detectors is shown, it will be appreciated by a person skilled in the art that preferred embodiments of the present invention may be equally applied to PET scanners with multiple pairs of detectors. Further, some embodiments of the invention may be applied to PET scanners having an uneven number of individual planar detectors, such as three detectors.

The PET scanner at rest may be described with reference to a stationary XYZ reference frame, where Y is the rotation axis of the detectors, and X and Z are perpendicular thereto. When the detectors are rotated, their position is preferably described with reference to a rotating frame of reference $X_R Y_R Z_R$, rotated by an angle of $\phi$ around the $Y_R$ axis, which axis is aligned with the Y axis of the XYZ reference frame (in FIG. 2, $\phi$ is about 90 degrees). The $X_R$ axis is made parallel to the planes of detectors 12 and 14 and the $Z_R$ axis is made perpendicular to the detectors. Each of the detectors 12 and 14 has a local two-dimensional coordinate system associated therewith, $X_1 Y_1$ associated with detector 12 and $X_2 Y_2$ associated with detector 14. Each detector is at a distance r from the Y axis.

As can be appreciated there are many possible problems in the alignment of the system, including, the Y and $Y_R$ axes not being aligned, $X_1$ not being parallel to $X_2$, $Y_1$ not being parallel to $Y_2$, the detectors being shifted in the X and/or Y directions, relative to each other and/or relative to the XYZ reference frame. However, the inventors have determined that only a few of the many possible misalignments tend to account for most of the error, especially after the SPECT alignments and/or the single-photon corrections are applied to the PET system.

In accordance with a preferred embodiment of the invention, a plurality of gamma ray pairs are acquired, preferably, from a plurality of rotation angles $\phi$. Then a set of optimal correction/calibration factors are determined, which yield a minimum error and/or maximum image quality. In accordance with a preferred embodiment of the invention, the optimal set of correction factors is determined using a mathematical optimization method.

When a radiation event occurs at point source 10, having a location $\vec{V}s_R = \{xs_R, ys_R, zs_R\}$, two gamma rays 16 and 18 are created, each traveling in an opposite direction. Ray 16 interacts with detector 14 at coordinates $\vec{V}2_R = \{x2_R, y2_R, (z2_R = -r)\}$ and ray 18 interacts with detector 12 at coordinate $\vec{V}1_R = \{x1_R, y1_R, (z1_R = r)\}$. The line connecting these two locations is the Line of Flight (LOF). In an ideal situation, all the LOFs pass through point source 10. However, due, in part, to the following imperfections, the LOFs calculated from the radiation-detector interaction points do not pass exactly through the provided position of the point source 10:

(a) imperfect geometrical alignment;
(b) imperfect planar resolution of the detectors;
(c) varying (probabilistic) depth of interaction of the gamma ray with the detector;
(d) imprecise knowledge of the rotation angle;
(e) imprecise knowledge of the point source location; and
(f) the gamma ray pair is not exactly collinear.

Since, in practical situations, most of these imperfections cannot be absolutely overcome, the distance between any given LOF and the point source location, denoted as "closest impact distance" (CID), will be non-zero.

In a preferred embodiment of the invention, the criterion for good calibration is that the RMS of the CID for a plurality of LOFs, at a plurality of rotation angles, is minimized and/or below a predetermined distance. To this end, the data need only be acquired once, stored in list mode and then manipulated, until an optimal correction is found.

In a preferred embodiment of the invention, the LOFs are represented as follows, although it should be appreciated than many other representation methods may be used as well:

Each detector can be aligned with respect to six degrees of freedom: three of rotation and three of translation. In a general form, the alignment (rotation and translation) may be represented as $T_a$, where a subscript "a" is used to denote an aligned variable:

$$\vec{V}_{Ra} = T_a(dx_R, dy_R, dz_R, d\phi_x, d\phi_y, d\phi_z) * \vec{V}_R \quad (1)$$

The alignments and rotations preferably comprise standard rotation and translation matrixes. A particular set of alignment factors may is preferably designated by:

$$\eta = (dx_R, dy_R, dz_R, d\phi_x, d\phi_y, d\phi_z) \quad (2)$$

Thus, $\eta_1$ is the set of factors for one detector and $\eta_2$ is the set for a second detector.

In the static XYZ reference frame, $\vec{V}_a = T\phi * \vec{V}_{Ra}$, where $T\phi$ is the transformation from the $X_R Y_R Z_R$ frame to the XYZ frame by counter rotation by $\phi$. The LOF is then represented parameticly, using a factor t, between $\vec{V}1_a$ and $\vec{V}2_a$, so that the closest encounter with point source 10 may be determined from the equation of the LOF:

$$\vec{V}_a(t) = (\vec{V}1_a + \vec{V}2_a)/2 - (\vec{V}1_a - \vec{V}2_a) * t, \text{ where } -0.5 <= t <= 0.5. \quad (3)$$

The CID ($|\vec{V}_a(t)-\vec{V}_s|$) can be minimized, by solving:

$$\frac{d}{dt}|\vec{V}_a(t)-\vec{V}_s|^2 = 0 \quad (4)$$

so that, by differentiating and expressing for CID:

$$CID^2 = \left|\frac{\vec{V}1_a + \vec{V}2_a}{2} - \vec{V}s\right|^2 - \frac{\left[\left(\frac{\vec{V}1_a + \vec{V}2_a}{2} - \vec{V}s\right)\cdot(\vec{V}1_a - \vec{V}2_a)\right]^2}{|\vec{V}1_a - \vec{V}2_a|^2} \quad (5)$$

The sum of $CID^2$ for all the LOFs, which implicitly also includes a plurality of rotation angles is then defined as:

$$\delta^2 = \sum_{events} CID^2 \quad (6)$$

It should be noted that $\delta^2$ is a function of fifteen factors, generally denoted as $\{P\}$: $\vec{V}s$(3 factors), $\eta_1$(6 factors) and $\eta_2$(6 factors). By optimizing $\delta^2(P)$ with respect to all its factors, it is possible to determine optimal values both for the calibration factors and for the point source location.

Thus, in a preferred embodiment of the invention, the calibration process is as follows:

(a) Determine and perform single photon-type corrections. SPECT type alignments are usually performed during the initial installation of the camera, however, they may be repeated periodically.

(b) Acquire a plurality of pairs of events, preferably at a plurality of rotational positions of the detectors. Preferably, the angular positions at which the events are acquired are evenly distributed over an angular range of $2\pi$, or multiples thereof. Alternatively, the data is acquired over a smaller range of angles, such as $\pi$. The events are preferably acquired with a maximal possible accuracy and stored in list mode, so that various factor corrections may be applied. In some preferred embodiments of the invention, at least one of the point sources is aligned with the axis of rotation. Alternatively, especially when only one point source is used, this source is not aligned with the axis of rotation. It should be noted that the exact position of point source 10 does not need to be known, it can be determined from the LOFs.

(c) Set the initial value of the calibration factors ($\eta_1$ and $\eta_2$) to zero.

(d) Determine an estimate for $\vec{V}s$ {xs, ys, zs}, by solving the following three linear coupled equations, using the initial estimate for $\eta_1$, $\eta_2$:

$$\partial\delta^2/\partial xs=0;\ \partial\delta^2/\partial ys=0;\ \partial\delta^2/\partial zs=0 \quad (7)$$

(e) Calculate $CID^2$, using the determined $\vec{V}^s$. Preferably, ignoring events having exceptionally large $CID^2$, such as those exceeding a predetermined distance and/or LOFs further than two standard deviations. Typically, these extreme events result from photon scattering and/or random occurrences.

(f) Determining a best fit for the acquired data, using the initial $\vec{V}^s$, $\eta_1$ and $\eta_2$. Preferably, the process is repeated iteratively, until $\delta^2$ is minimal and/or stable to a predetermined degree, such as a few parts per million. Preferred types of best fit and/or iterative methods may be found in "Numerical Recipes in C", 2nd edition, by S. A. Teukolsky, W. T. Veterrling, and B. P. Flannery, Cambridge Univ. Press, Cambridge, 1992.

(g) Thereafter, the resulting values for $\eta_1$ and $\eta_2$ may be used to correct future acquired acquisition data. As can be appreciated, there is usually a tradeoff between image reconstruction time and data correction. Thus, in a preferred embodiment of the invention, at least some of the calibration corrections are performed on the data after a user decides to obtain higher quality images. These corrections are preferably performed on data which is stored in list mode.

It should be appreciated that not all the factors need be fitted. Rather, in some preferred embodiments of the invention, only a small number of factors are allowed to vary and the rest of the factors are held at zero or at some other predetermined value. In one preferred embodiment of the invention, if some of the calibration factors have small values they are clamped to zero, to increase the quality of the fit of the other factors. For example, if the angular dislocations are found to be very small, such as below 0.2 degrees, they are preferably clamped to zero, to make the linear corrections better and/or converge faster. Further, not all dimensions need to be calibrated. Thus, in one preferred embodiment of the invention, only the transaxial dimension is calibrated. Alternatively or additionally, not all the coordinates of the point source need to be determined, for example, only the (x, y) coordinates may be determined in one preferred embodiment of the invention. Partial calibration and/or point source estimation are especially useful in a system in which one dimension and/or calibration factor are either more precise and/or more stable than in other dimensions. Alternatively, it may be possible to calibrate the other dimensions using other faster and/or more precise and/or lower cost techniques.

In a preferred embodiment of the invention, incremental correction is practiced, in which a previous set of correction factors are used as a starting point for the new set of factors.

Incremental calibration is further described in PCT application PCT/IL97/00217, filed Jun. 29, 1997 by applicant Elscint Ltd. and titled "Gamma Camera with Incremental Calibration" published as WO 98/19179, now U.S. application Ser. No. 09/297,239, the disclosure of which is incorporated herein by reference and is especially useful when it is desirable to repeat the calibration of the PET system periodically. In one example, not all of the factors are calculated during each calibration procedure, rather only those factors which are known to vary are re-fit.

As described above, not all factors are equally important for correcting errors in the calibration. One particular factor which has been found to be important is $(dx1_R+dx2_R)/2$. It should be noted that many factors appear only in particular combinations, for example, $dx1_R$ and $dx2_R$ appear only as a sum and a difference. In another example, $dy1_R$ and $dy2_R$ appear only as a difference $y_{12}=dy1_R-dy2_R$. Thus, as a correction value, $dy1_R$ is set to $y_{12}/2$, and $dy2_R$ is set to $-y_{12}/2$.

In the above discussion, the CID has been treated as a single value. However, in many cases it is useful to independently consider axial and transaxial components of the CID. In a particular example, it is assumed that the PET system has perfect angular alignment:

$$d\phi 1_x=0;\ d\phi 1_y=0;\ d\phi 1_z=0;\ d\phi 2_x=0;\ d\phi 2_y=0;\ d\phi 2_z=0; \quad (8)$$

In such a case, the optimization function $|CID|^2$ splits into two components:

$$|CID|^2=|CID_T|^2+|CID_Y|^2 \quad (9)$$

where $|CID_T|^2$ is confined to the transverse plane (X, Z) and $|CID_Y|^2$ is parallel to the axis of rotation (y). The following discussion concentrates on the transverse component.

A point source is positioned in the fixed coordinate system at location $\vec{V}s=\{xs, zs\}$; $rs\{\sin(\phi s), \cos(\phi s)\}$, in polar coordinates. The detectors rotate at radii $r1=r+dr1$; $r2=r+dr2$. At a system rotation angle $\phi$, a coincident pair is detected at $x1_R$ and $x2_R$, hence $\vec{V}1_R=\{x1_R, (z1_R=r+dr1)\}$ and $\vec{V}2_R=\{x2_R, (z2_R=-(r+dr2))\}$. By defining the following substitutions:

$$\Delta x = \frac{dx1_R + dx2_R}{2} \quad dx = \frac{dx1_R - dx2_R}{2} \quad (10)$$
$$\Delta r = \frac{dr1 + dr2}{2} \quad dr = \frac{dr1 - dr2}{2}$$

and an angle $\alpha$, between the LOF and the $Z_R$ axis, hereafter referred to as the transverse angle:

$$\tan\alpha = \frac{x1_{Ra} - x2_{Ra}}{r1 + r2} = \frac{\frac{x1_R - x2_R}{2} + dx}{r + \Delta r}$$

$|CID_T|^2$ can be shown to be:

$$|CID_T|^2 = \cos^2\alpha\left[\frac{x1_R + x2_R}{2} + \Delta x - xs(\cos\varphi - \sin\varphi\tan\alpha) + ys(\sin\varphi - \cos\varphi\tan\alpha)\right]^2 \quad (11)$$
$$= \cos^2\alpha\left[\frac{x1_R + x2_R}{2} - \Delta x - rs(\sin(\varphi s - \varphi) - \cos(\varphi s - \varphi)\tan\alpha)\right]^2$$

Thus, the alignment parameters appear in the optimization function only as the combinations $\Delta x$, $dx$, $\Delta r$ and $dr$. The explicit form of $|CID_Y|^2$ may be similarly derived and only the axial alignment combination $dy=(dy1-dy2)/2$ appears therein.

The relative importance of the different factors may also be evaluated, using the above derived equations. In a particular case, it is assumed that data is acquired over $2\pi$ of rotation, evenly over the rotation. $|CID_T|^2$ is expanded to the first order in the alignment parameters and averaged over the rotation $\phi$ and the transverse angle $\alpha$. I.e.:

$$\langle\langle|CID_T|^2\rangle_\varphi\rangle_\alpha = \quad (12)$$
$$\int_{-\alpha\max}^{\alpha\max} d\alpha \varepsilon^2(\alpha)\left[\frac{1}{2\pi}\int_0^{2\pi}|CID_T|^2 d\varphi\right] \bigg/ \int_{-\alpha\max}^{\alpha\max} d\alpha \varepsilon^2(\alpha)$$

where $\alpha\max$ is the maximum transverse acceptance angle, limited either by the detector size or by software. $\varepsilon^2(\alpha)$ is the squared probability of the detector stopping power (photon detection efficiency), which is close to 1 in a high efficiency system and $\{opacity/\cos\alpha\}$ in a low efficiency system. The result of the averaging is:

$$\langle\langle|CID_T|^2\rangle_\varphi\rangle_\alpha \cong \quad (13)$$
$$\left[\Delta x^2 + \frac{1}{2}\left(\frac{rs}{r}\right)^2 dx^2\right]\langle\cos^2\alpha\rangle_\alpha + \left[dr^2 + \frac{1}{2}\left(\frac{rs}{r}\right)^2 \Delta r^2\right]\langle\sin^2\alpha\rangle_\alpha$$

The effect of the detectors being high efficiency or low efficiency is less than 10% when $\alpha\max \leq 40°$. In a typical system configuration, detector size and radius of rotation determine an $\alpha\max$ of about 35°. In this case, the cos term is about 0.88, while the sin term is about 0.12, i.e., the sin term is far outweighed by the cos term. As the value of $\alpha\max$ is decreased, the cos term increases in relative importance. Thus, in a preferred embodiment of the invention, $\alpha\max$ is made as small as possible, preferably 20°, 15°, 10° or even 5°. The optimal value for $\alpha\max$ is dependent on the event statistics, since for smaller $\alpha\max$ fewer events will be taken into account during calibration.

It should be noted that each of the cos and sin terms is composed of two elements, one of which cannot be evaluated if the point source is in the center of rotation, $rs=0$. Thus, in a preferred embodiment of the invention, at least one of the point sources is placed off center ($rs\neq 0$). For a typical value of $rs=r/2$ (the average occupation of a human body in the imaging volume) and an $\alpha\max=35°$, the $|CID_T|^2$ optimization expression can be evaluated as:

$$\langle\langle|CID_T|^2\rangle_\varphi\rangle_\alpha \cong 0.88\left[\frac{dx1_R + dx2_R}{2}\right]^2 + \quad (14)$$
$$0.11\left[\frac{dx1_R - dx2_R}{2}\right]^2 + 0.12\left[\frac{dr1 - dr2}{2}\right]^2 + 0.015\left[\frac{dr1 + dr2}{2}\right]^2$$

This explains why, a most important calibration factor is $(dx1_R+dr^2_R)/2$.

Another aspect of some embodiments of the present invention, relates to measuring and monitoring the quality of a nuclear medicine system. As noted above, one of the outputs of the calibration process is a determination of the location of the point source. In a preferred embodiment of the present invention, the linearity of a nuclear medicine system is assessed by positioning a point source within the imaging volume of the system in a controlled and known manner and comparing a calculated position with the known one. A comparison of the two positions yields a volumetric linearity map of the system, which can be used to assess the need to perform calibration, estimate expected distortions and image quality in the system and may also be used as a linearity map correction and/or to post process acquired images. It should be appreciated that such a linearity measurement may be used to determine the linearity of the system even in fewer than all the dimensions, for example, even in a single dimension.

In a preferred embodiment of the present invention, the above calibration process is used to assess the theoretical volumetric resolution of a nuclear medicine system. Typically, the theoretical resolution of a nuclear medicine system is assessed by reconstructing an image of a point source, a line source or a phantom. However, this reconstruction already includes errors caused by improper calibration and image reconstruction. Thus, it cannot be considered to be an upper limit on the resolution achievable with a particular system. In a preferred embodiment of the invention, it is noted that $|CID_T|^2$ and $|CID_Y|^2$ are actually the axial and transaxial variances of the LOF with respect to the point source. This provides an estimate of the potential volumetric and/or axial and/or transaxial resolving power of the nuclear medicine system.

As indicated above, in a preferred embodiment of the invention stray LOFs are removed from the data before performing the calibration calculations. It should be noted that there are typically two types of stray LOFs, one caused by scattering and another caused by random coincidences. Such events generate LOFs far removed from the point source, thereby diminishing the alignment sensitivity of the optimization procedure. In accordance with a preferred embodiment of the invention, the above calibration procedure is first performed with all the data including the stray data. Alternatively only stray data which is within some predetermined error criterion is used, such as within a predetermined distance and/or a certain number of standard deviations. Thereafter, the calibration process is repeated, without the strays to obtain an exact calibration. However, the first calibration is useful both for finding a good starting point for the second calibration step and/or for determining which calibration factors are important.

Figure 3:
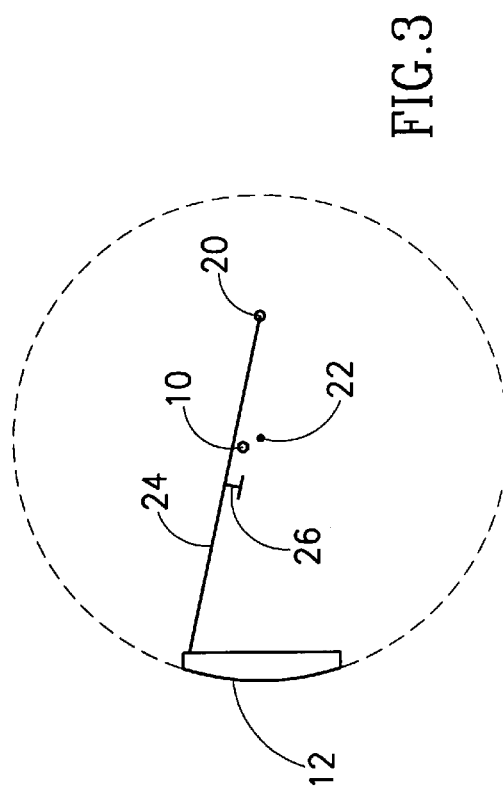
FIG. 3 is a schematic diagram of calibrating a fan beam for SPECT, in accordance with a preferred embodiment of the invention.

Another aspect of some preferred embodiments of the present invention relates to calibrating cone beam and fan beams, especially for SPECT. Focused SPECT geometries present a similar problem to PET alignment. Typically, a fan beam data set is converted into a parallel beam data set for reconstruction. However, such conversion requires a knowledge of calibration parameters which are typically determined by image reconstruction. FIG. 3 is a schematic diagram of calibrating a fan beam for SPECT, in accordance with a preferred embodiment of the invention. In FIG. 3, detector 12, including a fan beam collimator (not shown) rotates around a center of rotation 22. The collimator has a focal location 20. Point source 10, which is preferably not at the center of rotation, generates a gamma ray which is detected by detector 12. It should be noted that source 10 need not be a positron source. However, if source 10 is a positron source, this calibration method can be used to determine the relative alignment of focal locations of two opposing detectors. Alternatively, source 10 may be a light source.

An LOF 24 is formed between focal location 20 and the point of interaction of the gamma radiation with detector 12. Reference number 26 indicates the CID between the calculated LOF and the actual position of point source 10. By performing a calibration procedure as described above, it is possible to determine optimal calibration for one or more of the following parameters:

(a) center of rotation (22);

(b) focal location (20); and (c) point source location (10).

It should also be noted that the precision of the collimator is not usually a problem which needs to be calibrated for, since the collimators are usually very precisely machined, contain no moving parts and can be tested using light, which testing has a lower noise level than testing using ionizing radiation. However, the above optimization may also be used to correct collimator miss-machining, by comparing the relative determined focal location, for different locations on detector 12.

In a preferred embodiment of the invention, especially useful in focused SPECT calibration, the calibration procedure may performed on projection data rather than list mode data. Thus, although a reduction in precision may be expected, list mode data being more precise than projection data, a reduction in computation required may also be expected. All events in one pixel of detector 12 may be represented by a single LOF 24, and thus, a single value for $|CID|^2$. I.e.:

$$\sum_{events\ in\ rotation} |CID|^2_{event} \rightarrow \sum_{pixels\ in\ projections} count(pixel) \cdot |CID|^2_{pixel} \quad (15)$$

It should be noted that any type of focused SPECT geometries, such as a cone beam, may be calibrated using the above described method, however, for simplicity, only a fan beam is shown.

In accordance with a preferred embodiment of the invention, wobble of the focal line of a fan beam is determined by moving point source 10 in parallel to detector 12. Alternatively, a line source may be used.

Appendix "A" is a software listing for a program which is useful in performing calibration in accordance with one preferred embodiment of the invention. The definition file "clist.h" serves as an interface with the target machine, in this case a Varicam Acquisition Station Version 3.2. The software listing is to be compiled using a C compiler, preferably the "Visual Age" compiler for the OS/2 operating system.

Appendix "B" is a hexadecimal dump of an executable of the program, suitable for running on such a station: A Pentium® 133 MHz IBM compatible PC, using the OS/2 operating system Version 3.2. The dump was generated on a HP-UX version 9 operating system, using the command "od -x". The "*" symbols are used to indicate lines which are identical to a previous line. Thus, if there are four consecutive lines which contain the same data, only the first one is printed and a "*" symbol is printed instead of all the other lines. An indication of the position of the line in the file, at the leftmost column, can be used to reconstruct the number of missing lines.

It should be appreciated, that the present invention may be modified and applied on systems other than the simple PET system described. Modified systems to which the above described method of correction apply include systems with: any number, even or uneven, of detectors; detectors not positioned at symmetrical angular locations around the Y axis; detectors at uneven radii; linear moving detectors, in which case a plurality of point sources are preferably positioned along the axis of motion and or a collimator is used in conjunction with a line source; and systems where one or more of the detectors is reduced to a one dimensional detector (a fan beam) or a zero dimensional detector (a cone beam). Thus the present invention is not limited by what has thus far been described. Rather, the present invention is limited only by the claims which follow.

What is claimed is:

1. A method of calibrating a PET (Positron Emission Tomograph) scanner, comprising:

acquiring data from a plurality of coincidence radiation events, using at least one detector; and determining values for a set comprising at least one calibration factor, which factor affects an analytically defined calibration criterion.

2. A method according to claim 1, wherein said at least one detector comprises at least one rotating planar detector and wherein acquiring data comprises acquiring data from a plurality of rotational positions of the at least one detector.

3. A method according to claim 2, wherein said at least one rotating detector comprises two rotating detectors and wherein said rotating detectors rotate around an axis and wherein said at least one factor comprises a sum of linear translations of said two detectors along a transaxial direction.

4. A method according to claim 3, wherein said radiation emanates from a point source and impinges on said detectors at an input angle from said point source, relative to a line perpendicular to said axis and connecting said point source; said method comprising:

rejecting events response to said input angle.

5. A method according to claim 4, wherein said input angle comprises an axial component and wherein said rejecting comprises rejecting responsive to said axial component.

6. A method according to claim 4, wherein said input angle comprises a transaxial component and wherein said rejecting comprises rejecting responsive to said transaxial component.

7. A method according to claim 4, comprising limiting the allowed input angles, responsive to event statistics of the acquired data.

8. A method according to claim 2, comprising positioning one or more point sources in said PET scanner, wherein said radiation events occur substantially inside said point sources.

9. A method according to claim 2, comprising performing single-photon type corrections on said PET scanner, prior to acquiring said data.

10. A method according to claim 2, comprising estimating a position of a source of at least some of said radiation events from said acquired data.

11. A method according to claim 10, wherein said determining values comprises determining values responsive to said estimated position.

12. A method according to claim 1, wherein the criterion is an error criterion and wherein determining comprises optimizing said at least one factor to minimize the error criterion.

13. A method according to claim 12, wherein optimizing at least one factor comprises:

optimizing said first factor and at least a second factor; and clamping said second factor to zero, responsive to the determined values thereof.

14. A method according to claim 12, wherein optimizing comprises performing an iterative search.

15. A method according to claim 1, wherein determining comprises determining said value without user input.

16. A method according to claim 1, wherein determining comprises:

determining said values using said data; and repeating said determining with a subset of said data, said subset not including at least some stray radiation events, said repeating utilizing said determined values in said repeated determination.

17. A method of calibrating a focused single-photon system, comprising:

acquiring data from a plurality of radiation events, generated by a single radiation source, said acquiring using at least one rolating detector; and determining values for a set comprising at least one calibration factor, which factor affects an analytically defined calibration criterion, wherein determining said values comprises optimizing the calibration with respect to at least one of a center of rotation or said system, a focal location of said system and a location of the radiation source.

18. A method according to claim 17, wherein said optimization comprises minimizing a calculated distance between a location of said radiation source and a line connecting said focal location and said at least one detector.

19. A method according to claim 18, wherein said radiation source is a point source.

20. A method according to claim 17, wherein said focused system has a fan geometry.

21. A method according to claim 17, wherein said focused system has a cone geometry.

22. A method of calibrating an event counting medical imaging system, comprising:

acquiring data from a plurality of radiation events, using at least one detector; and determining values for a set comprising at least one calibration factor; and repeating said determining with a subset of said data, said subset not including at least some stray radiation events, utilizing said determined values in said repeated determination.

23. A method according to claim 22, wherein said factor affects an analytically defined calibration criterion.

24. A method of measuring volumetric linearity of a nuclear medicine system, comprising:

positioning at least one radiation point source;

acquiring data from a plurality of radiation events, generated by said at least one point source, using at least one detector;

determining a location of said point source from said radiation events;

repeating said positioning, said acquiring and said determining for at least a second position of said radiation source;

comparing said determined locations and the positions of the point source; and determining a volumetric linearity of said system based on results of said comparison.

25. A method according to claim 24, wherein said point source comprises a positron source.

26. A method according to claim 25, wherein said radiation events comprise coincidence events.

27. A method of determining a potential resolution, along at least one dimension, of an event counting nuclear medicine system, comprising:

acquiring data from a plurality of radiation events, generated by a radiation source, using at least one detector; and determining a calculated distance, in said dimension, between a path determined for a radiation event and the location of the radiation source, for a plurality of radiation events.

28. A method according to claim 27, wherein said radiation events comprise coincidence events.

29. A method according to claim 28, wherein said determined path connects determined interaction positions of components of a single coincidence event.

30. A method according to claim 27, wherein said determined path connects a focal location of a collimator associated with said at least one detector and an interaction position of said radiation event on said detector.

31. A method according to claim 27, wherein said radiation source comprises at least one point source.

32. A method according to claim 27, wherein said at least one detector rotates around an axis.

33. A method according to claim 32, wherein said at least one dimension comprises a transaxial dimension.

34. A method according to claim 32, wherein said at least one dimension comprises an axial dimension.

* * * * *